United States Patent [19]

Jaicks

[11] Patent Number: 4,641,662
[45] Date of Patent: Feb. 10, 1987

[54] ENDOCERVICAL CURETTE SYSTEM

[76] Inventor: John R. Jaicks, 945 Morris Park Ave., Bronx, N.Y. 10462

[21] Appl. No.: 655,378

[22] Filed: Sep. 28, 1984

[51] Int. Cl.⁴ ............................................. A61B 10/00
[52] U.S. Cl. ..................................................... 128/757
[58] Field of Search ............................... 128/305–318, 128/749–759; D24/28; 30/136, 340, 342; 220/265, 266, 281, 273, 298, 301; 215/250, 332

[56] References Cited

U.S. PATENT DOCUMENTS

| 1,573,681 | 2/1926 | Dareaux | 128/314 |
| 2,577,406 | 12/1951 | Crandell | 30/340 |
| 3,509,879 | 5/1970 | Bathish et al. | 220/266 |
| 3,640,268 | 2/1972 | Davis | 128/757 |
| 3,796,211 | 3/1974 | Kohl | 128/757 |
| 3,845,872 | 11/1974 | Towns et al. | 220/281 |
| 3,927,783 | 12/1975 | Bogert | 215/332 |
| 4,149,651 | 4/1979 | Ignell | 220/265 |
| 4,384,587 | 5/1983 | Milgrom | 128/757 |
| 4,482,073 | 11/1984 | Gagliardi | 215/332 |

FOREIGN PATENT DOCUMENTS 872548 3/1962 United Kingdom ................ 128/757

OTHER PUBLICATIONS

"Gynecological Instruments", Surgical Instruments, 1973 Novak (90–6292).
"New Biopsy Instruments", Biomed. Eng. 1980, Aksenova et al.
"Endometrial Biopsy Currettes and Vulvar Biopsy Punches".
"Carethage in the Diagnosis of Cervical Cancer", The Lancet, Anderson, 1951.

Primary Examiner—Edward M. Coven
Assistant Examiner—Max F. Hindenburg
Attorney, Agent, or Firm—Lackenbach Siegel Marzullo & Aronson

[57] ABSTRACT

A curette system for scrapping the endocervix in performing an endocervical curettage (ECC) procedure. The system includes a disposable curette scraper removably mounted to the end of an elongated handle. The curette scraper includes an elongated wall having a curved base end and curved tapered edges extending between the base and a tip portion. The wall and its edges are adapted to fit over the cervix up to the anatomical internal os. Serrations are formed along each tapered edge. The curette scraper is plastic and can be removed from the handle and placed in a fixative along with the tissue and mucus scrapings for pathological analysis.

12 Claims, 13 Drawing Figures

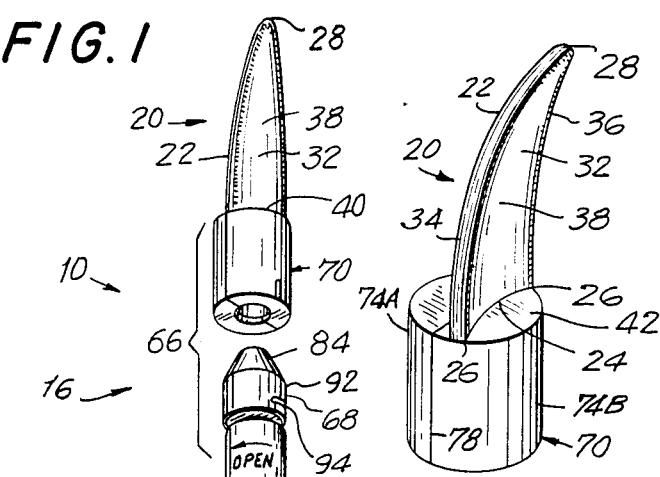
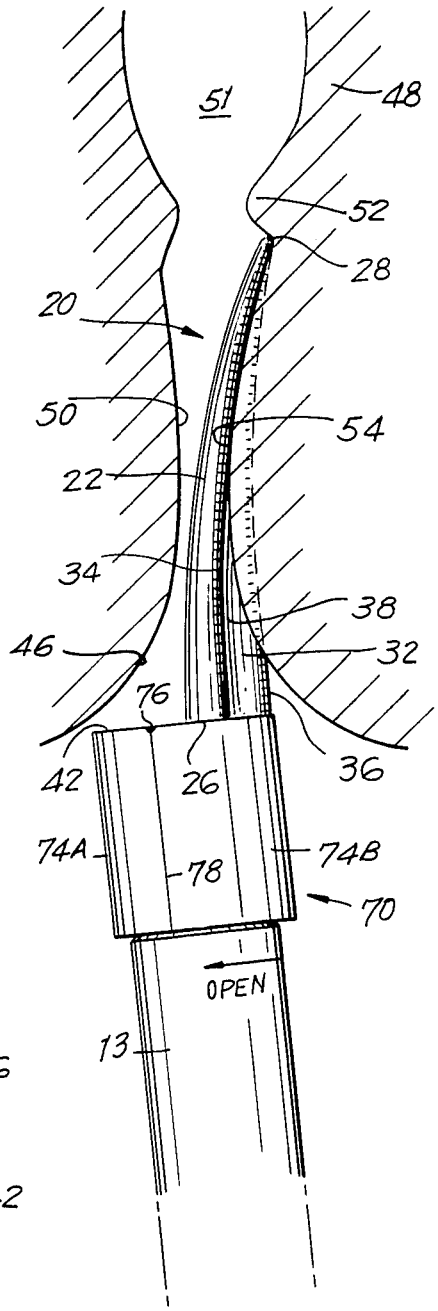
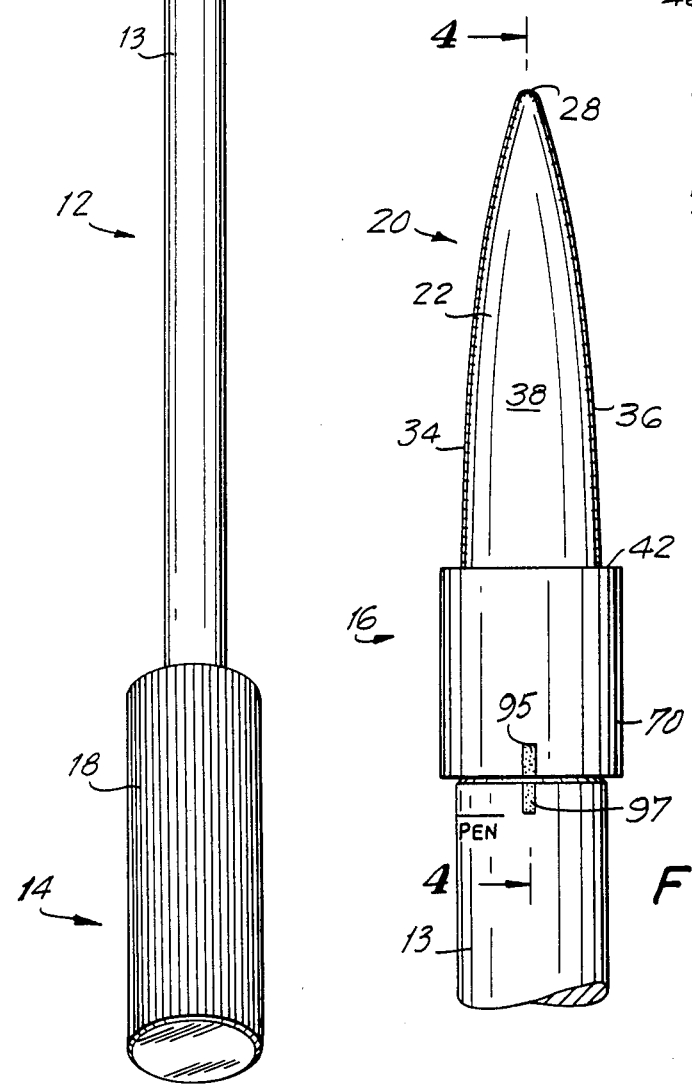

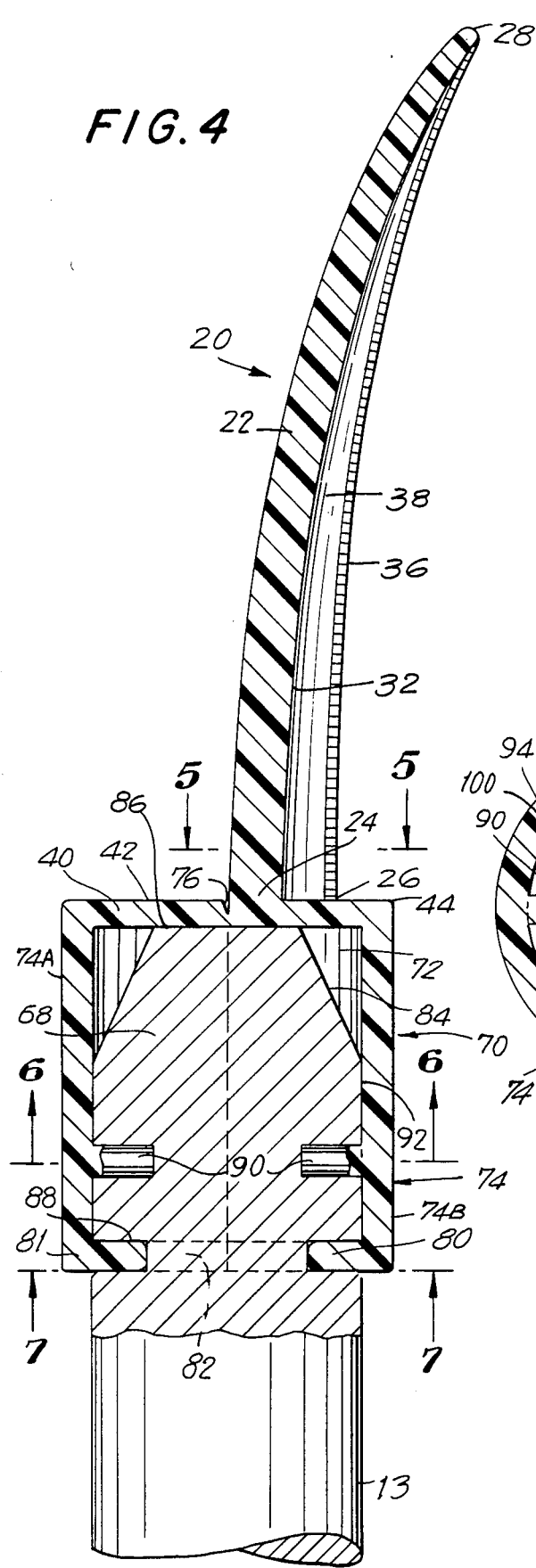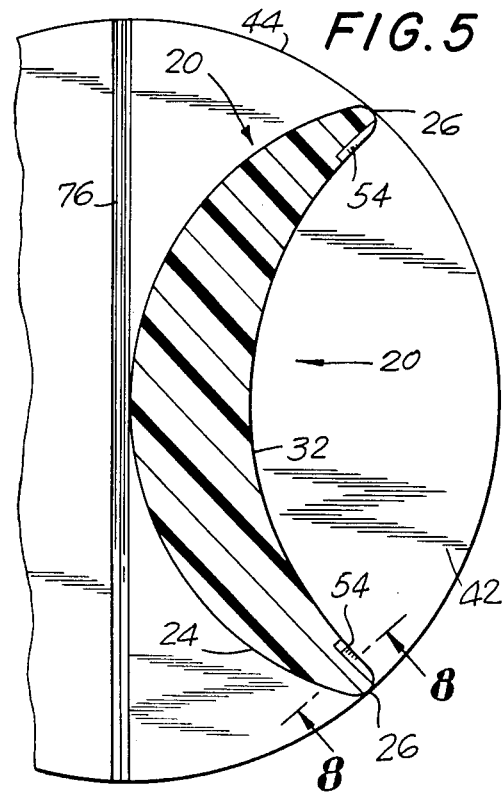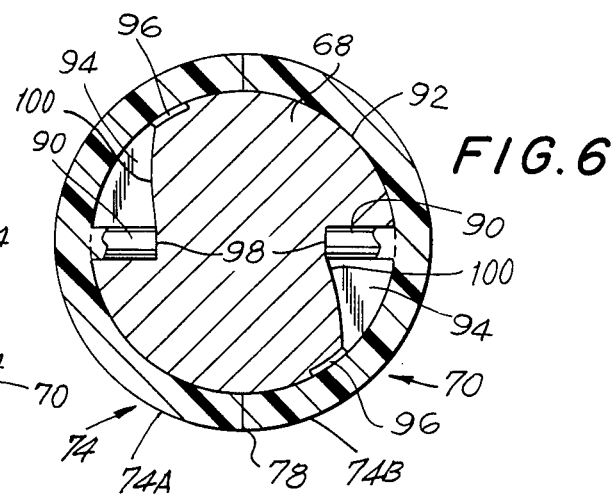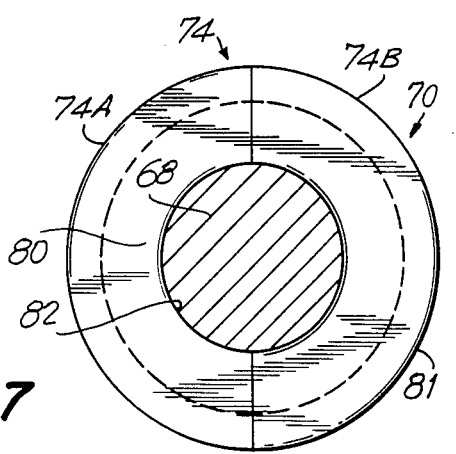

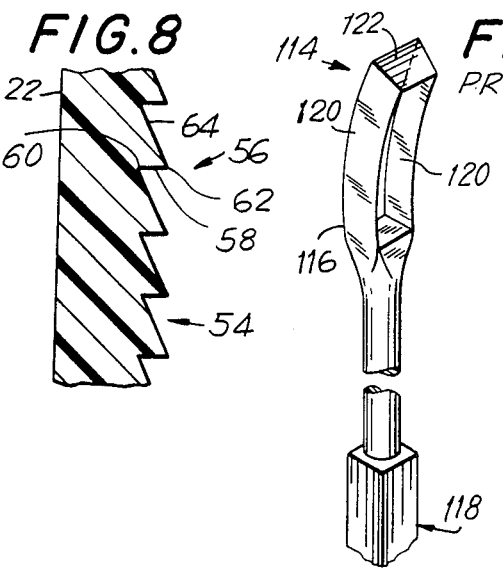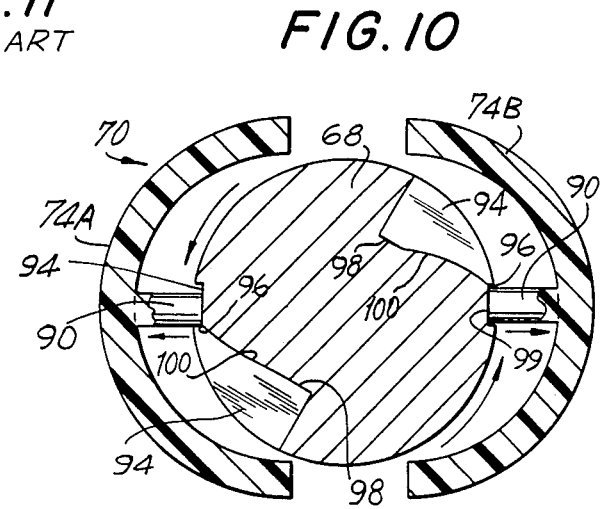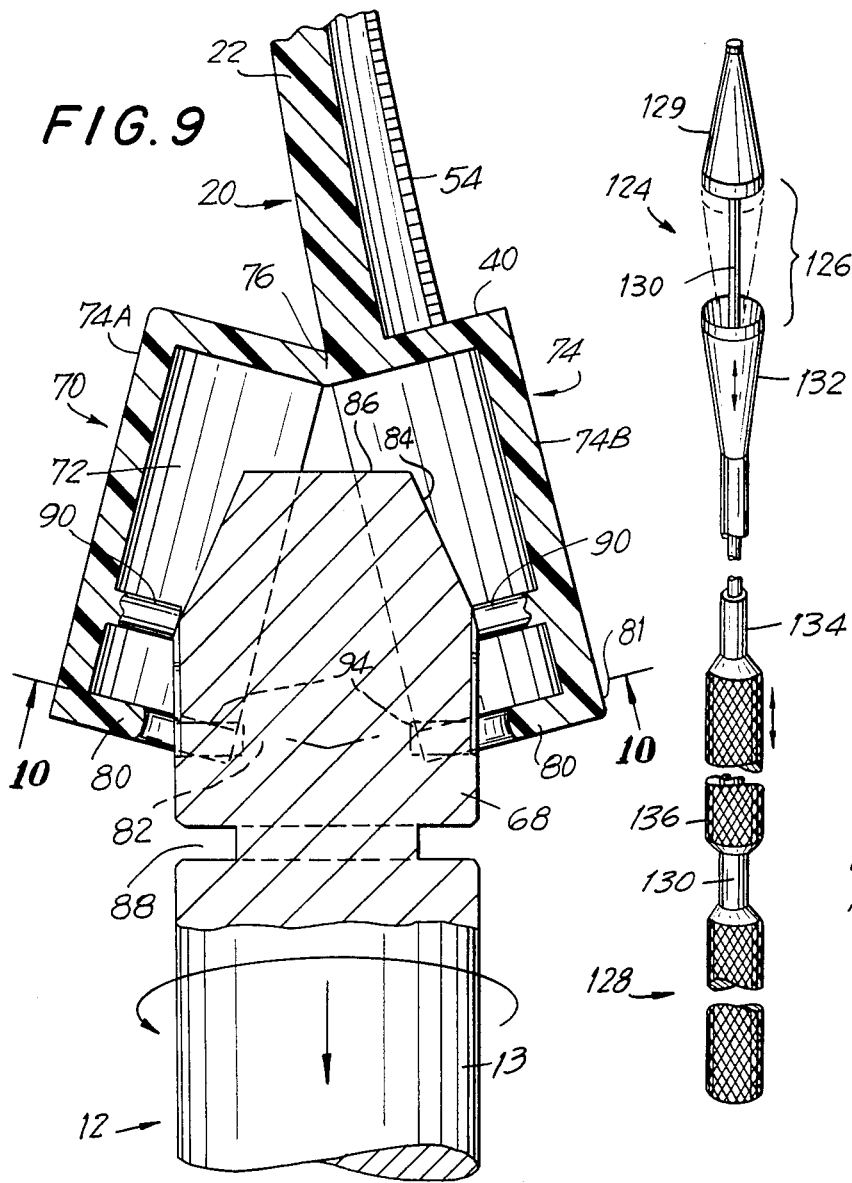

ENDOCERVICAL CURETTE SYSTEM

BACKGROUND OF THE INVENTION

This invention relates generally to an endocervical curette or endocervical scraper, for use both in detecting cervical cancer beyond the site of the colposcope and in all endoscopic examinations.

Detection of the cervix area for abnormal cell growth ranging from precancerous atypical dysplasia to invasive cancer is begun by first obtaining a pap smear of the area. It is paranthetically noted that the discussion herein relates to carcinoma or dysplasia only of the endocervix area and is generally not directed to diagnosis of cells of the vagina and vulva.

The cervix, which is the circular constricted area between the uterus and the vagina, presents particular problems for the gynecologist in the area up to the anatomical internal os, for it is in this area that the gynecologist has difficulty in directly observing even with instrumentation and where biopsy sampling and curettage, that is, gathering of tissue and mucus samples, is most problematical.

Upon information of a positive, or abnormal, pap smear, certain procedures relating to the cervix area of the patient are generally followed by the gynecologist. The procedures mentioned are as follows: observing the cervix with a magnifying colposcope, which makes suspicious areas in the transitional zone obvious to the physician; taking a biopsy of the suspicious areas with a fine instrument either as directed by the colposcope, or, if the upper areas of the cervix at or beyond the internal os are involved, taking the biopsy blindly; making an endocervical curettage (ECC) with a curette around the entire area of the cervix, up to the internal anatomical os. A pathologist examines the biopsied and curettaged samples to determine how atypical the cell samples are, that is, whether the cells reveal dysplasia, surface cancer (intraepithetial neoplasia, cin I, II, or III, or invasive cancer. With this information, the gynecologist proceeds with the proper treatment directed to removal of the abnormal cells.

The curettes used in the field for taking the curetted samples are the metal "G" curette and the "K" curette. These are illustrated in FIGS. 11 and 12 respectively and are discussed briefly in the detailed discussion below. Neither type of curette, in my opinion, possesses the structure that enables a gynecologist to ensure that an adequate curetted sample is obtained for the pathologist. This structural inadequacy lends itself, I believe, to small inaccuracies in the sampling procedure. The G curette forces the colopscopist to push and probe tissue from its crevices, and the K curette may miss a small strip of cells that could possibly include invasive cancer. The K curette also requires shaking tissue from the curette into the specimen bottle, which contains a fixative such as formaldahyde. Care must be taken that all the tissue and mucus taken from the endocervix during the ECC is shaken from the curette into the fixative. Both the G and K curettes also require a vaginal non-absorbent posterior sponge for mucus that may contain abnormal cells.

The ECC procedure is very important because the colposcopic examination is incomplete since approximately 14% of lesions picked up by the pap smear occur up to the internal os area, beyond the area seen in a colposcopic examination. There is a 5% reoccurrence of cancer after local treatment. This reoccurrence can be reduced to 0% if a curette can be devised that eliminates the inadequacies and inaccuracies of the presently used curettes.

It is noted that another difficulty in using present curettes is that every cervix differs in size according to age, the number of births, or menopausal situation, for example. Missing an invasive cervical cancer is a disaster: in six months an *invasive* cancer can progress rapidly.

It is very important that the gynecologist give the pathologist every iota of material to make possible a correct diagnosis for relatively hidden or obscure areas so that the patient is not subjected to a cone biopsy, which is extremely dangerous both at the time and in future reproductive years when, among other problems, mid-trimester abortions occur. Early dysplasia and/or carcinoma occurs even in girls 14 to 16 years of age, so every means should be taken to arrest this slow-moving disease before it becomes invasive. Once invasive, the consequences are devastating. Radiation therapy or radical surgery, even if successful in stopping the cancer, can still leave young women sexually crippled and/or sterile.

Accordingly, it is an object of the present invention to provide a disposable curette for performing an ECC that is superior to curettes known in the art.

It is a further object of the present invention to provide a disposable curette for an ECC that is capable of obtaining a complete tissue and mucus sample from the area of the cervix up to the internal os where viewing by the colposcope is impossible and tissue and/or mucus samples are not practically obtainable by currettage plus vaginal sponge or telfa placed posteriorly in the vagina.

It is still another object of the present invention to provide a disposable, non-absorbable curette for an ECC that can be removed from a handle and placed in toto in a jar of fixative with the biopsied material and non-absorbably pad, wasting no time and requiring little or no effort by the operator.

It is yet another object of the present invention to provide a removable curette for an ECC that is capable of scraping a complete or an almost complete revolution of the cervix in the area of the endocervix up to the internal os and placed in a fixative in toto.

It is yet another object of the present invention to provide a disposable curette for an ECC that is capable of providing a complete tissue and mucus sample by successive scrapings of removable curettes so that the total sample contains all areas of potential abnormal cells so that the pathologist is assured of having every sample of suspect tissue and mucus so that the chance of error is reduced to virtually or absolutely nil.

In order to achieve the above objects, as well as others that will become apparent hereafter, a curette apparatus is provided for scraping the cervix area of a patient in an endocervical curretage (ECC) procedure that includes an elongated handle member having a gripping and an opposed mounting end; a curette member removably connected to the mounting end of the handle member; and a locking apparatus for removably holding the curette member to the mounting end of the handle member in a captured position. The curette member is adapted to scrape tissue and mucus from the surface of the endocervix, up to the area of the internal os, and is also adapted to hold removed tissue and mucus upon removal of the curette member from the handle member.

The curette member includes an elongated wall having a curved base edge having base ends, a tip portion, and a pair of mating inwardly tapered edges extending between the base ends and the tip portion. The curved base wall is preferably formed over a 140° arc. The elongated wall includes an inner surface defining a hollow between the tapered edges and the base edge. A base wall having a flat top surface generally transverse to the elongated wall is secured to the curved base edge of the elongated wall, the base wall further defining the hollow. The base wall has an edge portion that is preferably circular and the base ends of the elongated wall of the curette member is generally coextensive with the edge portion. The elongated wall and the tapered edges define a slight curvature adapted to fit generally over the surface of the endocervix to the internal os. The curvature will vary according to a range of patterns that relate to different sizes and configurations of the cervixes of women of varying ages, sizes and conditions. The curvature is tilted inward, or toward, the hollow and the base wall.

The inner surface of the curette member forms a plurality of serrations at the tapered edges of the curette member; the serrations are slightly spaced from the tapered edges and lie generally on the inner side of the hollow formed by the inner surface. The serrations are adapted to move smoothly over the surface of the deep endocervix when the curette is moved inwardly into the cervix; to collect tissue and mucus when the curette member is firmly pressed against the endocervical tissue and pulled outwardly from the internal os to the ectocervix so as to remove a scraping and to prevent loss of even a single malignant focus of cells.

The locking apparatus includes a male member positioned at the mounting end of the handle member, and a female housing forming a locking chamber and extending from the base wall of the curette member. The female housing is capable of movement between open and closed positons wherein in the open position the male member is capable of movement into or from the chamber and in the closed position the male member is axially locked in the captured position. The female housing includes a cylindrical side wall extending downwardly from the rim of the circular base wall. The housing has a cylindrical side wall that comprises a pair of opposed half side walls that are joined at a diametrical groove formed across the top surface of the base wall. The half side walls are biasable apart to a distance that enables the male member to pass into or from the chamber. A circular tab that extends radially inward from the bottom rim of the cylindrical side wall is adapted to fit into a radial circular pocket formed by the male member. A pair of opposed dowels connected to the inner surface of each of the cylindrical half walls of the female housing extend transversely into the locking chamber and are adapted to fit into a pair of opposed axially aligned tracking slots formed in the male member that lead to a radial locking slot that has outer and inner slot portions joined by a slanted surface. When the dowels are at the outer slot portions and the male member and the female housing are rotated relative to one another, the dowels are moved in the slot to the inner slot portion so as to radially lock the male member with the female member and the curette member to the handle. The female housing is self-biased at the base wall so as to bias the two half side walls together.

The present invention will be better understood and the objects and important features, other than those specifically set forth above, will become apparent when consideration is given to the following details and description, which when taken in conjunction with the annexed drawings, describes, discloses, illustrates, and shows preferred embodiments or modifications of the present invention and what is presently considered and believed to be the best mode of practice in the principles thereof. Other embodiments or modifications may be suggested to those having the benefit of the teachings herein, and such other embodiments or modifications are intended to be reserved especially as they fall within the scope and spirit of the subjoined claims.

BRIEF DESCRIPTION OF THE DRAWINGS

FIG. 1 is an exploded perspective view of the handle member and the curette member of the present invention;

FIG. 1A is a perspective view of the curette member in isolation;

FIG. 2 is a partial sectional slightly turned side view of the curette member in the process of scraping the cervix of a patient;

FIG. 3 is a front view of the currette member as joined to the handle member;

FIG. 4 is a sectional side view of the curette member and the joining portions of the curette member and the handle member in the closed, or locked, position;

FIG. 5 is a view taken through line 5—5 of FIG. 4;
FIG. 6 is a view taken through line 6—6 of FIG. 4;
FIG. 7 is a view taken through line 7—7 of FIG. 4;
FIG. 8 is a view taken through line 8—8 of FIG. 5;
FIG. 9 is a sectional side view of the curette member and the joining portions of the curette member in the open position; and FIG. 10 is a view taken through line 10—10 of FIG. 9.

FIG. 11 is a fragmented perspective view of a prior art cervix scraper; and

FIG. 12 is a fragmented perspective view of a prior art cervix scraper used to take biopsies of selected areas.

DESCRIPTION OF THE PREFERRED EMBODIMENTS

Reference is now made specifically to the drawings in which identical or similar parts are designated by the same reference numerals throughout.

FIG. 1 is a perspective view of a curette system 10 that includes an elongated handle member 12 including an extended rod portion 13 having a gripping end 14 and an opposed mounting end 16. Handle member 12 is preferably made of a rigid material such as a lightweight metal or a plastic. Gripping end 14 is preferably provided with a hand-grip 18 preferably molded with handle member 12 but can be a separate slide-on grip made of an easily gripped material such as rubber. System 10 also includes a curette member 20, best seen in FIGS. 1A and 3, that has an elongated wall 22 having a curved base edge 24 having opposite base ends 26, a tip portion 28, which is rounded so as not to scratch the surface of the endocervix 20 (shown in FIG. 2), an inner surface 32 (FIG. 4), and a pair of mating, inwardly tapered edges 34 and 36 that extend between base ends 26 and tip portion 28. Inner surface 32 defines a hollow 38, best seen in FIG. 5. Curette member 20 includes circular base wall 40 having a flat top surface 42 that is secured to curved base edge 24 of elongated wall 22. Base ends 26 preferably are coextensive with the circular rim 44 of base wall 40. The portion of flat top surface 42 within the arc curved base edge 24 of elongated wall 22 further defines hollow 38. Curette member 20 is disposable and is preferably made of a flexible, but yet a strong and firm type plastic, or other rigid material having similar properties, such as metals or other alloys. In all cases, the curette is designed to be of the disposable type.

Before proceeding with the description of the preferred embodiment of the invention, a short description of the area of cervix 30 follows. The cervix, which as described previously, is the lowest region of the uterus 48 and provides a passage, or endocervical canal 50, between the vagina (not shown) and the uterine, or endometrial, cavity. The cervical opening into the vagina is called the external os 46 (side view). The cavity running the length of cervix 30 is the mentioned endocervical canal 50. The opening into endometrical cavity 51 is the internal os 52. External os 46 is particularly important to the present invention, for it is precisely this area of the endocervix upwards that prevents the gynecologist from clearly observing the surface of that portion of cervix 30 up to internal os 52 where *undetected* cancer by colposcopy, occurs most frequently.

Elongated wall 22 along with tapered edges 34 define a slight curvature adapted to fit generally over the surface of cervix 30 particularly past external os 46 up to internal os 52, as best seen in FIG. 2. The operation of curette member 20 in relation to the endocervix will be described later in detail. The slight curvature mentioned above is an inward curvature relative to hollow 38 flat surface 42 of base wall 40. As seen in the elevational cross-section of FIG. 4, the inward curvature is preferably great enough to extend tip portion 28 to a position past the vertical plane of rim 44 of base wall 40.

As seen in FIGS. 1, 1A, 2, 3, 4, and most clearly in FIG. 5, inner surface 32 of elongated wall 22 forms a plurality of serrations spaced slightly from and transversely opening on tapered edges 34 and 36. At this point, it is noted that tapered edges 34 and 36 are slightly rounded so as not to unduly irritate the walls of the endocervix since the purpose of the present invention is to obtain a good sampling of tissue and mucus of the endocervix.

Serrations 54 are preferably formed in the manner shown in the fragmentary elevational view of FIG. 8. Each individual serration 56 includes a first flat surface 58 generally transverse to elongated wall 22 and having an inner edge 60 and an opposed outer edge 62. Edges 60 and 62 are generally transverse to tapered edges 34 and 36. Each serration 56 further includes a second flat surface 64 that is angled both toward elongated wall 22 and tip portion 28. Second flat surface 64 has a top edge coextensive with inner edge 60 of first flat surface 58 and a lower edge coextensive with outer edge 62 of first flat surface 58. With this arrangement, serrations 54 are adapted to move smoothly over the surface of endocervix 50 with inward movement of curette member 20 into the cervix; to hold tissue and mucus when curette member 20 is removed slowly and firmly against endocervix 52, thereby retaining mucus and tissue when curette member 20 is removed firmly and smoothly from the endocervix.

Curette member 20 is removably locked to mounting end 16 of handle member 12 by a locking apparatus 66 seen in particular in FIGS. 1, 4, 9, and 10. Locking apparatus 66 includes a generally cylindrical male member 68 positioned at mounting and 16 of handle member 12 and a female housing 70 forming a locking chamber 72. Female housing 70 extends downwardly from the rim 44 of circular base wall 40 of curette member 20. Female housing 70 is capable of movement between an open position, as seen in FIG. 9, and a closed position as seen in FIG. 4. In the open position; male member 68 is capable of movement into or from chamber 72 and in the closed position male member 68 is capable of being locked in a captured position.

Female housing 70 includes a cylindrical side wall 74 secured to base wall 40, side wall 74 and base wall 40 in part defining locking chamber 72. Base wall 40 is made of a semi-rigid but flexible material such as a plastic. As noted before, base wall 40 is preferably circular and forms a diametrical groove 76. Cylindrical side wall 74 comprises a pair of opposed half side walls 74A and 74B joined at diametrical groove 76. Base wall 40 is flexibly movable along diametrical groove 76 between a first position as shown in FIG. 4 and a second position as shown in FIG. 9. In the first position, base wall 40 is flat and half side walls 74A and 74B are adjacent one another along mating surfaces 78 between base wall 40 so as to form locking chamber 72. A circular bottom tab portion 80 extending inwardly from the bottom rim 81 of side wall 74 of female housing 70 further defines locking chamber 72. Bottom tab 80 forms a central circular aperture 82 and is generally opposed to base wall 40. In the second position base wall 40 is bent at an acute angle relative to curette member 20 along diametrical groove 76 and half side walls 74 and 74B are spaced apart to a distance that enables male member 68 to pass into or from locking chamber 72 through the general area of aperture 82. It is noted that male member 68 is preferably formed with a circular taper 84 that extends downwardly from top wall 86 of male member 68. Taper 84 enables male member 68 to enter chamber 72 with somewhat less of a spacing apart between half side walls 74 and 74B being necessary.

Male member 68 forms a circular pocket 88 spaced from its top wall 86 that is capable of receiving circular tab 80 within aperture 82 when female member 68 is in the closed position seen in FIG. 4.

As best seen in FIG. 4, male member 68 has a cylindrical outer surface 92. Male member 68 forms a pair of oppositely positioned locking slots 94 extending inwardly from surface 92. Locking slots 94 each include an outer slot area 96 and an inner slot area 98 spaced inwardly from outer slot area 96. Locking slots 94 are disposed on a radial plane relative to male member 68. A pair of axially aligned positioning slots 99 extend from the top portion of male member 68 at taper 84 along outer surface 92 to outer slot area 96 of locking slots 94. Locking slots 94 are adapted to slidingly receive and guide dowels 96 to final locking positions at inner slot areas 98. Slots 94 form slanted surfaces 100 between outer and inner slot areas 96 and 98. Female housing 70 and male member 68 are capable of being rotated relative to one another when male member 68 is positioned in locking chamber 72 when female housing 70 is in the closed position shown in FIGS. 4, 6 and 7. When male member 68 is pressed into locking chamber 72 through aperture 82, tracking slots 92 are aligned with dowels 90 by way of aligning slot-dowel markers 95 and 97 respectively on male member 68 and female housing 70 so that when the male member 68 is pressed inwardly, dowels 90 are guided along the positioning slots 99 to enter outer slot areas 96 so that half walls 74A and 74B of female housing 70 pressed apart into the unlocked position seen in FIGS. 9 and 10. At this point, dowels 90 are also in their unlocked position. Male member 68 and female housing 70 are then rotated relative to one another with male member 68 being rotated clockwise as viewed in FIG. 10 so that dowels 90 move over slanted surface 100 to inner slot areas 98 and assume the positions shown in FIG. 6. When dowels 90 lock into locking slot 94 so as to firmly hold female housing 70 in an axial lock mode.

FIG. 10 illustrates a releasing action where male member 68 has been rotated clockwise so that dowels 90 have been moved from their locked mode of FIG. 6 at inner slot areas 98 to their unlocked mode at outer slot areas 96. This rotational movement of male member 68 and female housing 70 relative to one another so as to move dowels 90 to their unlocked position also causes female half-housings, or half side walls, 74A and 74B to spread apart into the unlocked position of female housing 70 and to place housing 70 in an axial unlocked mode. This allows curette member 20 to be easily drawn from handle member 12 and thereupon placed in a fixative for later separation and analysis by the pathologist. In the locked dowel position shown in FIGS. 4, 6 and 7, male member 68 cannot be slid from female housing 70 unless the rotational movement described is performed. It is noted that in the operation and use of the curette system 10 of the present invention, the doctor is instructed to employ a smooth introductory movement of curette member 20 up the surface of the endocervix 50 and up to internal os 52 in order to scrape tissue and mucus from the entire area of the endocervix in a manner theoretically not to lose a single group of cells.

In operation, the gynecologist first places mounted curette member 22 into the vagina of the patient and against the surface of endocervix 50 including the area up to internal os 52 so that the cruve of the curette, that is, tapered edges 34 and 36 with serrations 54, are firmly pressed to the cervix surface at a first position that can be designated here as "6 o'clock" of an actual 360° circle or "clockface" formed by endocervix 50. Tip portion 28 is adapted to also perform a sample gathering function. The gynecologist then proceeds to take a series of scrapings. The curette member 20 enables a complete overlapped scraping to be accomplished with a minimum of three passes using three separate curettes. The preferred procedure or modus would be to commence scrapings at 6 o'clock and finish scraping at 2 o'clock and 10 o'clock. Here, each scraping would cover approximately 140° so as to overlap adjacent scrapings by about 10° on either side of the previous curettage. Of course, the series of scrapings may comprise any number of passes the pathologist desires, as it is the pathologist who bears the ultimate responsibility to the patient and gynecologist. From a practical point of view, no more than four, five or even six passes would be necessary. Obviously, the more passes, the greater the accuracy, but such action would subject the patient to a longer period of time for the procedure and additional discomfort to the patient. Should four passes be employed, four curette members 20 are required and each pass would cover an area of about 110° so as to provide approximately a 10° overlap on either side of the previous curettage.

By commencing at the 6 o'clock position and working around from both sides to the 12 o'clock, the doctor would have no bleeding and better visibility and orientation in the areas or zones to be scraped.

Thus, after each scraping, the gynecologist removes the curette member from the cervix area and the vagina. Each curette member 20 which includes female housing 70, is then removed from rod portion 13 by the doctor who without touching or otherwise disturbing the tissue and mucus on the cutting surface of the curette member 20 by rotating handle member 12 relative to female housing 70 which is held by the doctor so as to readily and easily open housing half-walls 74A and 74B apart via pressure from dowels 90. This simultaneously frees male member 68 so it can be axially slid from female housing 70. Thereupon, the gynecologist places the removed curette member 20 in a jar of fixative. The gynecologist then easily places a second curette member 20 upon handle member 12 by pressing half-walls 74A and 74B apart by the pressure of pushing tapered end 84 of male member 68 against tabs 80 and dowels 90. Thus male member 68 enters housing 70 at tracking slots 92 upon aligning of slot-dowel markers 95 and 97 and rotating male member 68 relative with housing 70 after positioning dowels 90 in locking slots 94 so as to allow dowels 90 to be biased inwardly in locking slots 94 from outer slot areas 96 to inner areas 98. Base wall 40, as is curette member 20 as a whole, is made of a biasable plastic material so that base wall 40 is self-biased at diametrical groove 76 and in turn biases half-walls 74A and 74B from the open position of female housing 74 seen in FIG. 9 to the closed position of housing 74 seen in FIG. 7. The gynecologist completes the diagnostic procedure by firmly pressing the second and third or any additional curette members, if employed, against the endocervical surface in the aforementioned manner.

FIGS. 11 and 12 illustrates in fragmented perspective views two types of prior art ECC sampling devices common in the profession, namely, a "G" curette and a cone-biopsy instrument respectively discussed earlier. The "G" curette 114 of FIG. 11 comprises a metal curette member 116 unitary with and positioned at the end of an elongated handle 118. Curette member 116 includes a pair of spaced opposed flat scrapers 120 that are curved to fit over the cervix area of the patient. A flat angled top wall 122 joins scrapers 120. In the pathologist's laboratory, tissue and mucus to be studied is scraped from the curette by a mode best taught to the technician by the individual pathologist and placed in a fixative prior to fabricating slides of the tissue and mucus.

ECC instrument 124 shown in FIG. 12 illustrates a cutting member 126 unitary with and positioned at the end of a elongated handle 128. The cutting member 126 has an outer cone-shaped portion 127 that is affixed to the end of immobile shaft 130. An inner cone-shaped portion 132 is secured to the end of movable shaft 134, which is slidably mounted over immobile shaft 130 so that movement of movable shaft 134 via gripping portion 136 of shaft 134 presses or withdraws the base of inner cone-shaped portion 132 into or from contact with the base of outer cone-shaped portion 128. Outer and inner cone-shaped portions 128 and 132 form hollow interiors with their bases forming openings to the interiors so that tissue and mucus is blindly obtained about presumptively the entire circumference of the endocervix upon each push/pull pass of the tool. Samples not dislodged or lost by falling off the instrument are then placed in a fixative after wiping clean in a most fastidious fashion by picking and shaking the cutting member 126 and cone portions 127 and 132, as well as that portion of the rod 130 which may have adherent tissue and mucus cells removed from the endocervix. This wiping action is generally done after each pass to collect a specimen in toto.

In each of the prior art devices illustrated in FIGS. 11 and 12, the doctor is removing the collected material and placing it in a container having a fixative. Such a procedure lends itself to considerable error in that it is impossible to remove in a reasonable time frame the entire tissue and mucus specimen from the instrument for any one single pass. This is a serious drawback and disadvantage as such devices can only be at most considered a screening procedure. It should be recognized that even the loss of a single group of cells can result in a disastrous outcome for a patient where invasion is missed as even if a subsequent later examination is done, the spread of cancer would already have penetrated more deeply and widely and advanced to a later, more irreversible stage of the disease.

It should be noted that the gynecologist in using any ECC tool must penetrate to a depth or "bite" of at least 2 mm, which is mandatory on the surface and in each crypt. The device of the present invention is capable of making such bites without excessive pressure or expertise on the part of the operator.

The embodiment of the invention particularly disclosed and described hereinabove is presented merely as an example of the invention. Other embodiments, forms, and modifications of the invention coming within the proper scope and spirit of the appended claims will, of course, readily suggest themselves to those skilled in the art.

What is claimed:

1. A curette system for scraping a patient in an endocervical curettage (EEC) procedure, comprising, in combination, an elongated handle member having a gripping end and an opposed mounting end, and curette means removably connected to said mounting end of said handle member, said curette means being for scraping and holding tissue and mucous from the surface of said endocervix up to the area of the internal os and not the area beyond the internal os, said curette means including a disposable curette member with an elongated wall having a curved base end like wall of about 140° arc, a tip portion, and a pair of mating inwardly tapered edges extending between said curved base and tip portion, said elongated wall having an inner surface defining a hollow between said tapered edges, serration means at said tapered edges of said curette member being for moving smoothly over the surface of the endocervix when the curette member is moved into the cervix, for holding mucous and tissue when said curette member is firmly scraped outwardly along the endocervix, and for retaining tissue and mucous when the curette member is removed from the endocervix, said serration means being spaced slightly inwardly toward said hollow and away from said tapered edges and comprising a plurality of serations, said plurality of serrations having a first flat surface transverse to said inner surfaces of said elongated wall said first flat surface having an inner edge coextensive with said elongated wall and an opposed outer edge, said inner and outer edges being generally transverse to said tapered edges, each of said plurality of serrations further including a second flat surface angled both toward said elongated wall and said tip portion, and a second flat surface having a top edge coextensive with said inner edge of said first flat surface and a lower edge coextensive with said outer edge of said first flat surface, and locking means for holding said curette means to said mounting end of said handle member, whereby said serration means is capable of gathering and retaining tissue and mucous scraped and pulled from over a wide area defined by said tapered curette member from the surface of the endocervix and the internal os as said curette member is removed from the endocervix by a drawing motion while firmly scraping outwardly along the endocervix in a non-rotatable movement, so as to in about a minimum of three passes using like, but separate and disposable curette members with an overlap on either side of a previous curretage cover the entire circumferential area of said endocervix, and whereby each disposable curette member being for analysis without any further handling.

2. A curette instrument according to claim 1, further including a circular base wall having a flat top surface generally transverse to said elongated wall and secured to said curved base end of said elongated wall, said base wall further defining said hollow, said circular base wall having a rim, said base end of said elongated wall of said curette member being generally co-extensive with said rim.

3. A curette instrument according to claim 2, wherein said elongated wall with said tapered edges defines a slight curvature adapted to fit generally over the surface of said endocervix and the internal os.

4. A curette instrument according to claim 3, wherein said curvature is inward relative to said hollow and said flat surface of said base wall.

5. A curette instrument according to claim 2, wherein said elongated wall defines a slight curvature adapted to fit generally over the surface of said cervix at the os and downward of the internal os and over the surface of the endocervical portion of the uterus.

6. A curette instrument according to claim 5, wherein said curvature is first inward then outward relative to said hollow and said flat top surface of said circular base wall, whereby the curvature is adapted to hug both the convex curvature at the internal os of the uterus and the concave curvature of the endocervical canal, respectively.

7. A curette system for scraping a patient in an endocervical curretage (EEC) procedure comprising, in combination, an elongated handle member having a gripping end and an opposed mounting end, and curette means removably connected to said mounting end of said handle, said curette means being for scraping and holding tissue and mucous from the surface of said endocervix up to the area of the internal os and not the area beyond the internal os, said curette means including a curette member with an elongated wall having a curved base end, a tip portion, and a pair of mating inwardly tapered edges extending between said curved base end and said tip portion to define with said elongated wall a slight curvature adapted to fit generally over the surface of said endocervix and and the internal os, said elongated wall having an inner surface defining a hollow between said tapered edges, said curette member further including a circular base wall further defining said hollow and having a flat top surface generally transverse to said elongated wall and being secured thereto at said curved base end, said circular base wall having a rim, said base end of said elongated wall of said curette member being generally coextensive with said rim, said curvature being first inward then outward relative to said hollow and said flat top surface of said circular base wall so that the curvature is adapted to hug the convex curvature at the internal os and the concave curvature of the endocervical canal, serration means at said tapered edges of said curette member being for moving smoothly over the surface of the endocervix when the curette member is moved into the cervix, for holding mucous and tissue when said curette member is firmly scraped along the endocervix, and for retaining tissue and mucous when the curette member is removed from the endocervix, said serration means being spaced slightly inwardly toward said hollow and away from said tapered edges and comprising a plurality of serrations, said plurality of serrations having a first flat surface transverse to said inner surface of said elongated wall, said first flat surface having an inner edge coextensive with said elongated wall and an opposed outer edge, said inner and outer edges being generally transverse to said tapered edges, each of said plurality of serrations further including a second flat surface angled both toward said elongated wall and said tip portion, said second flat surface having a top edge coextensive with said inner edge of said first flat surface and a lower edge coextensive with said outer edge of said first flat surface, and locking means for holding said curette member to said mounting end of said handle member, said locking means including a male member positioned at said mounting end of said handle member, and a female housing forming a locking chamber and extending from said base end of said curette member, said female housing being capable of movement between an open position and a closed position, wherein in the open position said male member is capable of movement into or from said locking chamber and wherein in the closed position said male member is actually locked in said captured position, said female housing including a cylindrical side wall secured to said circular base wall of said curette member, said cylindrical side wall and said base wall in part defining said locking chamber, and wherein said circular base wall is made of a biasable material and is circular, said flat top surface forming a diametrical groove and said cylindrical side wall comprises a pair of opposed half side walls joined at said diametrical groove, said base wall being biasedly movable along said diametrical groove between a first position and a second position wherein in the first position said base wall is flat and said half side walls are adjacent and said female member is in said closed position, and wherein in the second position said base wall is bent in a biased mode along said diametrical groove and said pair of opposed half side walls are biased apart to a distance that enables said male member to pass into or from said locking chamber.

8. A curette instrument according to claim 7, wherein said curved base edge of said elongated wall in approximately coextensive with said diametrical groove.

9. A curette instrument according to claim 8, wherein said cylindrical side wall includes a circular bottom rim opposite said base wall, said female housing further including a circular tab extending inwardly from said bottom rim, said tab forming a circular aperture, said tab further defining said chamber, and wherein said male member has a top wall and further forms a circular pocket spaced from said top wall capable of receiving said circular tab within said aperture when said female housing is in said closed position.

10. A curette instrument according to claim 9, wherein said female housing further includes a pair of oppositely positioned dowels extending transversely inwardly into said chamber from each of said half side walls between said base wall and said circular tab when said female housing is in said closed position; and wherein said male member is cylindrical and forms a pair of oppositely disposed radially aligned slots having outer slot areas proximate to said cylindrical surface and inner slot areas spaced inwardly from said outer slot areas, said male member forming slanted surfaces between said inner and outer slot areas; said female housing and said male member being capable of being rotated relative to one another when said male member is positioned in said chamber between a dowel unlocked position and a dowel locked position, wherein in said dowel unlocked position said pair of dowels are positioned at said outer slot areas and said female housing is in said unlocked position, and in said dowel locked position said pair of dowels are positioned at said inner slot areas and said female housing is in said axially locked position, whereby the male member can be removed from its captured position in the female housing by rotating the male member in a rotational direction that moves the dowels from the inner slot to the outer slot.

11. A curette instrument according to claim 10, wherein said male member includes an end portion and forms a pair of axially aligned tracking slots extending between said end portion and said outer slot areas, said tracking slots being capable of receiving said dowels and guiding them to said outer slot areas.

12. A curette instrument according to claim 11, wherein said end portion forms a tapered portion and said tracking slots extend between said tapered portion and said outer slot areas.

* * * * *